United States Patent
Bao et al.

[11] Patent Number: 5,976,186
[45] Date of Patent: *Nov. 2, 1999

[54] HYDROGEL INTERVERTEBRAL DISC NUCLEUS

[75] Inventors: Qi-Bin Bao, Livingston; Paul A. Higham, Ringwood, both of N.J.

[73] Assignee: Stryker Technologies Corporation, Kalamazoo, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/670,140

[22] Filed: Jun. 25, 1996

Related U.S. Application Data

[63] Continuation of application No. 08/303,297, Sep. 8, 1994, abandoned.

[51] Int. Cl.⁶ .......................................... A61F 2/44
[52] U.S. Cl. ................................ 623/17; 623/16; 623/18; 623/20
[58] Field of Search ................................ 623/16, 17, 18, 623/20, 21

[56] References Cited

U.S. PATENT DOCUMENTS

| | | | |
|---|---|---|---|
| 3,607,848 | 9/1971 | Stoy et al. | 623/66 |
| 3,867,728 | 2/1975 | Stubstad et al. | 623/17 |
| 3,875,595 | 4/1975 | Froning | 623/17 |
| 4,309,777 | 1/1982 | Patil | 3/1.91 |
| 4,331,783 | 5/1982 | Stoy | 525/294 |
| 4,337,327 | 6/1982 | Stoy | 525/280 |
| 4,349,921 | 9/1982 | Kunz | 3/1 |
| 4,369,294 | 1/1983 | Stoy | 525/340 |
| 4,370,451 | 1/1983 | Stoy | 525/294 |
| 4,379,874 | 4/1983 | Stoy | 524/27 |
| 4,420,589 | 12/1983 | Stoy | 525/93 |
| 4,631,188 | 12/1986 | Stoy et al. | 424/81 |
| 4,663,358 | 5/1987 | Hyon et al. | 521/64 |
| 4,714,469 | 12/1987 | Kenna | 623/17 |
| 4,772,287 | 9/1988 | Ray et al. | 623/17 |
| 4,863,477 | 9/1989 | Monson . | |
| 4,904,260 | 2/1990 | Ray et al. | 623/17 |
| 4,911,718 | 3/1990 | Lee et al. | 623/17 |
| 5,047,055 | 9/1991 | Bao et al. | 623/17 |
| 5,171,280 | 12/1992 | Baumgartner | 623/17 |
| 5,192,326 | 3/1993 | Bao et al. | 623/17 |
| 5,314,478 | 5/1994 | Oka et al. | 623/18 |
| 5,458,643 | 10/1995 | Oka et al. | 623/17 |
| 5,534,028 | 7/1996 | Bao et al. | 623/17 |
| 5,578,086 | 11/1996 | Prescott | 623/16 |
| 5,645,592 | 7/1997 | Nicolais et al. | 623/16 |
| 5,855,619 | 1/1999 | Caplan et al. | 623/16 |

FOREIGN PATENT DOCUMENTS

| | | |
|---|---|---|
| 0 356 112 | 2/1990 | European Pat. Off. . |
| 0453393 | 3/1991 | European Pat. Off. . |
| 0 505 634 | 9/1992 | European Pat. Off. . |
| WO-A 9210982 | 7/1992 | WIPO . |
| 9423671 | 10/1994 | WIPO ............ 623/17 |

*Primary Examiner*—Paul B. Prebilic
*Attorney, Agent, or Firm*—Lerner, David, Littenberg, Krumholz & Mentlik, LLP

[57] ABSTRACT

An article for use in the preparation of a hydrogel prosthetic nucleus, for an intervertebral disc, having equilibrium water contents (EWCs) of from about 30 to about 90% and compressive strengths of at least 4 meganewtons per square meter ($MNm^{-2}$), at their EWCs, when subjected to the same constraints as the normal nucleus, comprising one or more xerogel rods containing from zero to less than the EWC. A method for preparing a hydrogel prosthetic nucleus, for a vertebral disc, comprising one or more hydrogel rods containing from about 30 to about 90% water, and having compressive strengths of at least 1 $MNm^{-2}$, at their EWCs, which comprises inserting one or more hydrophilic xerogel rods, which at their EWC will contain from about 30 to about 90% water and have compressive strengths of at least 1 $MNm^{-2}$, containing water in an amount from about zero to less than their EWC, into the cavity of the disc through an opening in its annulus and allowing the rod, or rods, to absorb sufficient water from the body fluids to attain their EWCs and essentially fill the intervertebral nuclear disc cavity.

19 Claims, 2 Drawing Sheets

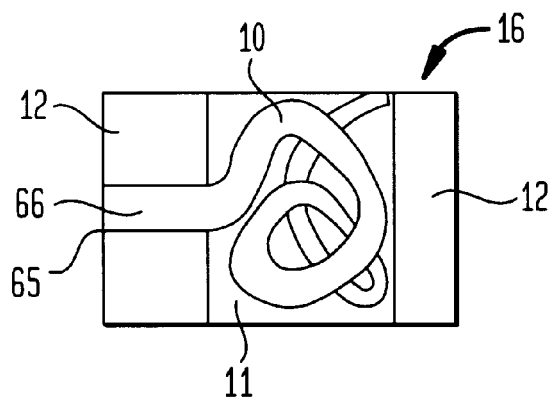
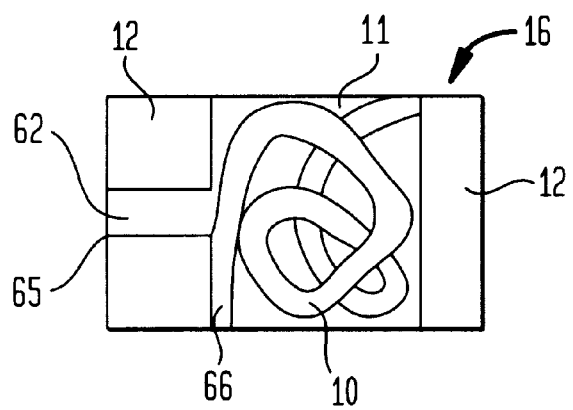
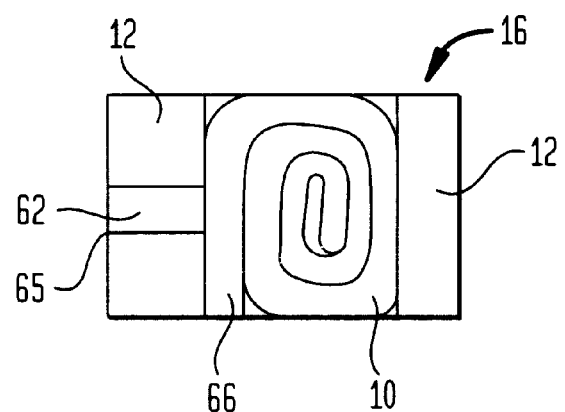

HYDROGEL INTERVERTEBRAL DISC NUCLEUS

This is a continuation of application Ser. No. 08/303,297, filed on Sep. 8, 1994, now abandoned.

BACKGROUND OF THE INVENTION

FIELD OF THE INVENTION

This invention relates to a prosthetic intervertebral disc nucleus. More particularly it relates to an artificial disc nucleus made of a hydrogel material.

The intervertebral disc is a complex joint anatomically and functionally. It is composed of three component structures: the nucleus pulposus (the nucleus), the annulus fibrosus (the annulus) and the vertebral end-plates. The biochemical composition and anatomical arrangements within these component structures are related to the biomechanical function of the disc.

The nucleus occupies about 25–40% of the total disc cross-sectional area. It is primarily composed of mucoid material containing mainly proteoglycans with a small amount of collagen. The proteoglycans consist of a protein core with chains of negatively charged keratin sulphate and chondroitin sulphate covalently attached thereto. Due to these constituents, the nucleus is a loose hydrogel which usually contains about 70–90% water by weight. Although the nucleus plays an important role in the biomechanical function of the disc, the mechanical properties of the disc are not well known, largely because of the loose hydrogel nature of the nucleus.

As the nucleus is surrounded by the annulus and vertebral end-plates, and the negatively charged sulphate groups are immobilized due to the attachment of these groups to the polymer matrix, the matrix has a higher concentration of counter ions than its surroundings. This ion concentration results in a higher osmotic pressure than the annulus e.g., ranging from about 0.1 to about 0.3 MPa. As a result of the high fixed charge density of the proteoglycan the matrix exerts an osmotic swelling pressure which can support an applied load in much the same way as air pressure in a tire supports the weight of a car.

It is the osmotic swelling pressure and hydrophilicity of the nucleus matrix that offers the nucleus the capability of imbibing fluid until it is balanced with the internal resistance stresses, due to the tensile forces of the collagen network, and the external stresses due to the loads that are applied by muscle and ligament tension. The swelling pressure (Ps) of the nucleus is directly dependent on the concentration and fixed charge densities of proteoglycan, i.e., the higher the concentration and fixed charge densities of proteoglycan the higher will be the swelling pressure of the nucleus. The external pressure changes with posture. When the human body is supine the compressive load on the third lumbar disc is 300 newtons (N) which rises to 700 N when an upright stance is assumed. The compressive load increases, yet again, to 1200 N when the body is bent forward by only 20°. When the external pressure (Pa) increases the previous balance, i.e., Ps=Pa, is upset. To reach a new balance the swelling pressure has to increase. This increase is achieved by increasing the proteoglycan concentration in the nucleus which is achieved by reducing the fluid in the nucleus. That is why discs lose about 10% of their height, as a result of creep, during the daytime. When the external load is released i.e., Ps is greater than Pa, the nucleus will imbibe fluid from its surroundings in order to reach the new equilibrium value. It is this property of the nucleus that is mainly responsible for the compressive properties of the disc.

The annulus forms the outer limiting boundary of the disc. It is composed of highly structured collagen fibers embedded in an amorphous base substance which is also composed of water and proteoglycans. The amount of proteoglycans is lower in the annulus than in the nucleus. The collagen fibers of the annulus are arranged in concentric laminated bands or lamella, (about 8–12 layers thick) with a thicker anterior wall and thinner posterior wall. In each lamella, the fibers are parallel and attached to the superior and inferior vertebral bodies at an angle of about 30° from the horizontal plane of the disc in both directions. This design particularly resists twisting because the half of the fibers cocked in one direction will tighten as the vertebrae rotate relative to each other in the other direction. *The composition of the annulus along the radial axis is not uniform. There is a steady increase in the proportion of collagen from the inner to the outer sections of the annulus. This difference in composition may reflect the need of the inner and outer regions of the annulus to blend into very different tissues while maintaining the strength of the structure. Only the inner lamellae are anchored to the end-plates forming an enclosed vessel for the nucleus. The collagen network of the annulus restrains the tendency of the nucleus gel to absorb water from surrounding tissues and swell. Thus, the collagen fibers in the annulus are always in tension, and the nucleus gel is always in compression.

The two vertebral end-plates are composed of hyaline cartilage, which is a clear, "glassy" tissue, that separates the disc from the adjacent vertebral bodies. This layer acts as a transitional zone between the hard, bony vertebral bodies and the soft disc. Because the intervertebral disc is avascular, most nutrients that the disc needs for metabolism are transported to the disc by diffusion through the end-plate area.

The intervertebral joint exhibits both elastic and viscous behavior. Hence, during the application of a load to the disc there will be an immediate "distortion" or "deformation" of the disc, often referred to as "instantaneous deformation". It has been reported that the major pathway by which water is lost, from the disc during compression, is through the cartilage end-plates. Since the water permeability of the end-plates is in the range of about 0.20 to about $0.85 \times 10^{-17}$ $m^4 N^{-1} sec^{-1}$ it is reasonable to assume that under loading, the initial volume of the disc is constant while the load is applied. Because the natural nucleus of the disc is in the form of a loose hydrogel, i.e., a hydrophilic polymeric material which is insoluble in water, it can be deformed easily, the extent of deformation of the disc being largely dependent on the extensibility of the annulus. It is generally believed that the hydrostatic behavior of the nucleus plays an important role in the normal static and dynamic load-sharing capability of the disc and the restoring force of the stretched fibers of the annulus balances the effects of the nucleus swelling pressure. Without the constraint by the annulus, annular bulging of the nucleus would increase considerably. If the load is maintained at a constant level, a gradual change in joint height, commonly referred to as "creep", will occur as a function of time. Eventually, the creep will stabilize and the joint is said to be in "equilibrium". When the load is removed the joint will gradually "recover" to its original height before loading. The creep and relaxation rates depend on the amount of load applied, the permeability of the end-plates and the water binding capability of the nucleus hydrogel. Creep and relaxation are essential processes in pumping fluid in and out of the disc.

Degeneration of the intervertebral disc is believed to be a common cause of final pathological changes and back pain. As the intervertebral disc ages it undergoes degeneration. The changes that occur are such that, in many respects, the composition of the nucleus seems to approach that of the inner annulus. Intervertebral disc degeneration is, at least in part, the consequence of compositional changes in the nucleus. It has been found that both the molecular weight and the amount of proteoglycans in the nucleus decrease with age, especially in degenerated discs, and the ratio of keratin sulphate to chondroitin sulphate in the nucleus increases. This increase in the ratio of keratin sulphate to chondroitin sulphate and decrease in proteoglycan content decreases the fixed charge density of the nucleus from about 0.28 meq/ml to about 0.18–0.20 meq/ml. These changes cause the nucleus to lose part of its water binding capability which decreases the maximum swelling pressure it can exert. As a result, the maximum water content drops from over about 85%, in preadolescence, to about 70–75% in middle age. The glycosaminoglycan content of prolapsed discs has been found to be lower, and the collagen content higher, than that of normal discs of a comparable age. Discs L-4-L-5 and L-5-S-1 are usually the most degenerated discs.

It is known that although the nucleus only occupies about one third of the total disc area, it takes about 70% of the total loading in a normal disc. Thus, it has been found that the compressive load on the nuclei of moderately degenerated discs is about 30% lower than in comparable normal discs but the compressive load on the annulus increases by 100% in the degenerated discs. This load change is primarily caused by the structural changes in the disc as discussed above. The excess load on the annulus, of the degenerated disc, causes reduction of the disc height and excessive movement of the spinal segments. The flexibility of the disc produces excessive movement of the collagenous fibers which, in turn, injures the fiber attachments and causes delamination of the well organized fibers of the annulus ring. The delaminated annulus can be further weakened by stress on the annulus and in severe cases this stress will cause tearing of the annulus. This whole process is very similar to driving on a flat tire, where the reinforcement layer will eventually delaminate. Because the thickness of the annulus is not uniform, with the posterior portions being thinner than the anterior portions, delamination and lesions usually occur in the posterior area first.

The spinal disc may also be displaced or damaged due to trauma or diseases. In these cases, and in the case of disc degeneration, the nucleus may herniate and/or protrude into the vertebral canal or intervertebral foramen, in which case it is known as a herniated or "slipped" disc. This disc may in turn press upon the spinal nerve that exits the vertebral canal through the partially obstructed foramen, causing pain or paralysis in the area of its distribution. The most frequent site of occurrence of a herniated disc is in the lower lumbar region. A disc herniation in this area often involves the inferior extremities by compressing the sciatic nerve.

There are basically three types of treatment currently being used for treating low back pain caused by injured or degenerated discs: conservative care, discectomy and fusion. Each of these treatments has its advantages and limitations. The vast majority of patients with low back pain, especially those with first time episodes of low back pain, will get better with conservative care treatment. However, it is not necessarily true that conservative care is the most efficient and economical way to solve the low back pain problem.

Discectomy usually provides excellent short term results in relieving the clinical symptoms, by removing the herniated disc material, usually the nucleus, which causes the low back pain either by compressing the spinal nerve or by chemical irritation. Clearly, a discectomy is not desirable from a biomechanical point of view. In a healthy disc, the nucleus takes the most compressional load and in a degenerated disc this load is primarily distributed onto the annulus ring which, as described above, causes tearing and delamination of the annulus. Removal of the nucleus in a discectomy actually causes distribution the compressive load onto the annulus ring thereby narrowing the disc spaces. It has been reported that a long-term disc height decrease might be expected to cause irreversible osteoarthritis-like changes in the facet joint. That is why discectomy yields poor long term benefits and results in a high incidence of reherniation.

Fusion generally does a good job in eliminating symptoms and stabilizing the joint. However, because the motion of the fused segment is restricted, the range of motion of the adjoining vertebral discs is increased possibly enhancing their degenerative processes.

Because of these disadvantages, it is desirable to use a prosthetic joint device which not only is able to replace the injured or degenerated intervertebral disc, but also can mimic the physiological and the biomechanical function of the replaced disc. Such a device would restore the normal functions of the disc and prevent further degeneration of the surrounding tissue.

DESCRIPTION OF THE PRIOR ART

Artificial discs are well known in the prior art. U.S. Pat. No. 3,867,728, to Stubstad et al., relates to a device which replaces the entire disc. This device is made by laminating vertical, horizontal or axial sheets of elastic polymer. U.S. Pat. No. 3,875,595 to Froning relates to a collapsible plastic bladder-like prosthesis of nucleus pulposus. U.S. Pat. No. 4,309,777, to Patil, relates to a prosthesis utilizing metal springs and cups. A spinal implant comprising a rigid solid body having a porous coating on part of its surface is shown in Kenna's U.S. Pat. No. 4,714,469. An intervertebral disc prosthesis consisting of a pair of rigid plugs to replace the degenerated disc is referred by Kuntz, U.S. Pat. No. 4,349,921. U.S. Pat. No. 4,772,287 and 4,904,260, to Ray et al., teach the use of a pair of cylindrical prosthetic intervertebral disc capsules with or without therapeutical agents. U.S. Pat. No. 4,911,718, to Lee et al., relates to an elastomeric disc spacer comprising three different parts; nucleus, annulus and end-plates, of different materials. At the present time, none of these inventions has become a product in the spinal care market. Bao et al., in U.S. Pat. Nos. 5,047,055 and 5,192,326 (assigned to the assignee of this invention and incorporated herein by reference) describe artificial nuclei comprising hydrogels in the form of large pieces shaped to conform to the shape of the disc cavity or beads within a porous envelope, respectively. The hydrogels have an equilibrium water content (EWC) of at least about 30% and a compressive strength of at least about 1 meganewtons per square meter (1 $MNm^{-2}$) when subjected to the constraints of the annulus and end plates of the disc. Preferably, the compressive strength of the nucleus is about 4 $MNm^{-2}$.

The primary disadvantage of the inventions of Stubstad et al., Patil, Kenna and Lee et al. is that use of their prostheses requires complete replacement of the natural disc which involves numerous surgical difficulties. Secondly, the intervertebral disc is a complex joint, anatomically and functionally, comprising the aforementioned three component structures, each of which has its own unique structural characteristics. Designing and fabricating such a complicated prosthesis from acceptable materials, which will mimic the function of the natural disc, is very difficult. A further problem is the difficulty of preventing the prosthesis from dislodging. Fourthly, even for prostheses which are only intended for replacing the nucleus, a major obstacle has been to find a material which is similar to the natural nucleus and is also able to restore the normal function of the nucleus. Hydrophobic elastomers and thermoplastic polymers are not desirable for use in the prosthetic nuclei due to their significant inherent differences from the natural nucleus e.g., lack of hydrophilicity, in the elastomers, and lack of flexibility in the thermoplasts.

These problems are not solved by Kuntz, who uses elastic rubber plugs, or by Froning and Ray et al., who use bladders, or capsules, respectively, which are filled with a fluid or thixotropic gel. According to the Ray and Froning patents, liquid was used to fill the capsules and bladders, respectively, thereby requiring that their membranes be completely sealed to prevent fluid leakage. As a consequence, those devices cannot completely restore the function of the nucleus which allows body fluid to diffuse in and out during cyclic loading thereby providing the nutrients the disc needs.

The Bao et al., prosthetic lumbar disc nuclei are made from hydrogels. Hydrogels have been used in biomedical applications, such as contact lenses. Among the advantages of hydrogels is that they are more biocompatible than hydrophobic elastomers and metals. This biocompatibility is largely due to the unique characteristics of hydrogels in that they are soft and contain water like the surrounding tissues and have relatively low frictional coefficients with respect to the surrounding tissues. The biocompatibility of hydrogels results in prosthetic nuclei which are more easily tolerated in the body. Furthermore, hydrophobic elastomeric and metallic gels will not permit diffusion of aqueous compositions, and their solutes, therethrough.

An additional advantage of some hydrogels is their good mechanical strength which permits them to withstand the load on the disc and restore the normal space between the vertebral bodies. The aforementioned nuclei of Bao et al. have high mechanical strength and are able to withstand the body loads and assist in the healing of the defective annuli.

Other advantages of the hydrogels, used in the Bao et al. nuclei, are their excellent viscoelastic properties and shape memory. Hydrogels contain a large amount of water which acts as a plasticizer. Part of the water is available as free water which has more freedom to leave the hydrogel when the hydrogel is partially dehydrated under mechanical pressure. This characteristic of the hydrogels enables them to creep, in the same way as the natural nucleus, under compression, and to withstand cyclic loading for long periods without any significant degradation or loss of their elasticity. This is because water in the hydrogel behaves like a cushion whereby the polymeric network of a hydrogel with a high EWC is less susceptible to damage under mechanical load.

Another advantage of hydrogels is their permeability to water and water-soluble substances, such as nutrients, metabolites and the like. It is known that body fluid diffusion, under cyclic loading, is the major source of nutrients to the natural disc. If the route of this nutrient diffusion is blocked, e.g., by a water-impermeable nucleus, further deterioration of the disc will ensue.

Hydrogels can be dehydrated and the resultant xerogels hydrated again without changing the properties of the hydrogels. When a hydrogel is dehydrated, its volume decreases, thereby facilitating implantation of the prosthetic nucleus into the nuclear cavity in the disc. The implanted prosthetic nucleus will then swell, in the body, by absorption of body fluid up to its EWC. The EWC of a hydrogel depends on the compressive load applied thereto. Thus, the EWC of a specific hydrogel in an open container will differ from the EWC of the same hydrogel in a closed vessel such as an intervertabral disc. The EWC values, referred to below, are for hydrogels subjected to compressive loads under the conditions found in an intervertebral disc. The expansion factor of a dehydrated hydrogel, in turn, is dependent on its EWC. Thus, it may vary from 1.19 for a hydrogel of 38% EWC to 1.73 for a hydrogel of 80% EWC. For an 80% EWC hydrogel, the volume of the dehydrated prosthetic nucleus is usually about 20% of that of the hydrated one. The ability to be dehydrated and then return to its original shape upon hydration, up to its EWC, makes it possible to implant the device posterior-laterally during surgery, thereby reducing the complexity and risk of intraspinal surgery as traditionally used. The danger of perforation of the nerve, dural sac, arteries and other organs is also reduced. In addition, the incision area on the annulus can be reduced, thereby helping to heal the annulus and prevent the reherniation of the disc. Hydrogels are also useful for drug delivery into the disc due to their capability for controlled release of drugs. Various therapeutic agents, such as growth factors, long term analgesics and anti-inflammatory agents can attach to the prosthetic nucleus and be released in a controllable rate after implantation of the nucleus in the disc.

Furthermore, dimensional integrity can be maintained with hydrogels having a water content of up to about 90%. This dimensional integrity, if the nucleus is properly designed, will aid in distributing the vertebral load to a larger area on the annulus ring and prevent the prosthetic nucleus from bulging and herniating.

However, it is normally difficult to implant a fully hydrated hydrogel prosthesis in the cavity, of a disc, through the small window provided in the disc, for removing the herniated nucleus, especially in a percutaneous surgery by virtue of their bulkiness in a fully hydrated state. Therefore, such prostheses must be implanted, in the disc in relatively dehydrated states which requires long periods to achieve their EWCs due to their low surface areas. Other hydrogels, having high surface areas, do not completely conform to the shape of the nuclear cavity.

It has been found that the hydrogel prosthetic nuclei of the present invention, and the method for their preparation, overcome the disadvantages of the prior art prosthetic nuclei.

SUMMARY OF THE INVENTION

In the following description of the invention the term "partially hydrated xerogel" refers to a hydrophilic xerogel which has absorbed water to an extent less than its EWC under its expected conditions of use.

The present invention relates to a hydrogel prosthetic nucleus which may be implanted in the nuclear cavity, of an intervertebral disc, as one or more xerogel rods or tubes which may be partially hydrated. The prosthetic nucleus of the invention may be brought to its EWC more rapidly than the hydrogel prostheses of the prior art due to its greater surface area and its ability to retain its shape without the support of a container such as the envelope required in the case of nuclei formed from hydrogel beads.

The prosthetic nucleus is prepared from one or more pieces of hydrophilic xerogel material, in the form of rods or tubes, which in their final, fully hydrated state, will essentially completely fill the nucleus cavity in the disc. Utilizing the hydrogel material in the form of the rod or tube facilitates implantation which can be effected with the nuclear material in a partially hydrated state.

One advantage of the prosthetic nuclei of the present invention is the decrease in the time for rehydration, in the body, by virtue of their high surface areas.

Other advantages of the invention are the lack of the need for forming the xerogel in the shape of the cavity or enclosing the xerogel, in the form of beads, in an envelope comprising a semipermeable membrane or inserting the prosthesis into the cavity in a dehydrated or nearly dehydrated state. The implant of the invention, to the contrary, may be inserted into the disc cavity in a partially hydrated state with the concomitant advantages enumerated above.

Thus, the prosthetic nucleus, of the present invention, may be inserted into the cavity in its partially hydrated form since the cross-sectional diameter of the partially hydrated rod is typically small, e.g., between about 2 and about 10 mm. However, if the diameter of the rod is too small it may be reextruded from the cavity upon the application of pressure thereto whereas a very large diameter would make implantation of the rod, through the window, difficult. Nevertheless, a slight excess in the diameter of the rod can be tolerated since, in the hydrated form, the diameter of the rod may be reduced by stretching. Furthermore, the probability of reextrusion of the implant is reduced since the implant comprises a long rod.

After hydration of the hydrogel tube or rod to its EWC, in the disc, the expanded tube or rod will essentially fill the cavity, from which the natural nucleus had been excised, and be constrained tightly therein by the annulus and end plates. The constraining forces are the restoring force of the stretched fibers of the annulus and the external force through the end-plates which will restrict the movement of the hydrogel nucleus and prevent it from bulging and herniating from the cavity.

Another advantage of this invention is the quick restoration of the biomechanical functions of the disc which depend on the degree of hydration of the implant.

It is an object of the invention to provide a prosthetic nucleus for a disc which functions in a manner similar to that of the natural nucleus.

It is yet another object of the invention to provide a prosthetic nucleus for a disc which is composed of a hydrogel material capable of balancing its hydrostatic pressure with external loads thereon.

It is another object of the invention to provide a prosthetic nucleus, as described above, wherein said hydrogel is implanted as a rod or hollow tube.

Another object of the invention is to provide a hydrogel prosthetic nucleus having an EWC, when subjected to the constraints of the annulus and end plates of the disc, of about 30 to about 90%, preferably about 60–80%, and a compressive strength of at least about 1 $MNm^{-2}$ under normal constraints wherein said prosthetic nucleus comprises one or more hydrogel rods or tubes. Preferably, the compressive strength of the nucleus is about 4 $MNm^{-2}$.

These and other objects and advantages of the present invention will become apparent from the following description and the accompanying drawings, which disclose a preferred embodiment of the invention. It is to be understood that the drawings are to be used for the purposes of illustration only and not as a limitation on the scope of the invention.

BRIEF DESCRIPTION OF THE DRAWINGS

In the drawings wherein similar reference characters denote similar elements throughout the several views:

FIG. 4 is an elevational view of the disc of FIG. 2 showing the prosthetic nucleus of the present invention in the partially hydrated state.

FIG. 5 is an elevational view of the disc and nuclear material of FIG. 3 wherein the tail end of the hydrogel rod has been inserted into the nuclear cavity.

FIG. 6 is an elevational view of the disc and nuclear material of FIG. 3 wherein the hydrogel has absorbed water, to its EWC, expanded to its maximum size and filled the nuclear cavity.

DESCRIPTION OF THE PREFERRED EMBODIMENT

Figure 1:
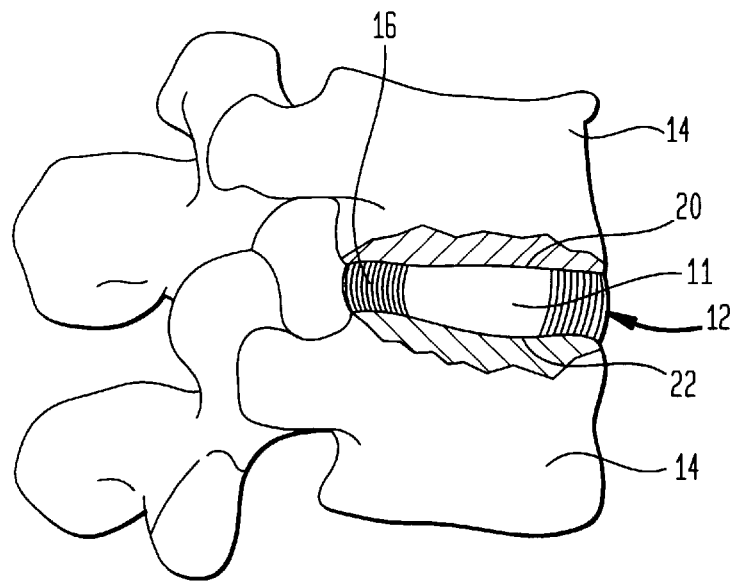
FIG. 1 is an elevational view, of the a vertebral disc, absent its nucleus, with its associated vertebrae.
Figure 2:
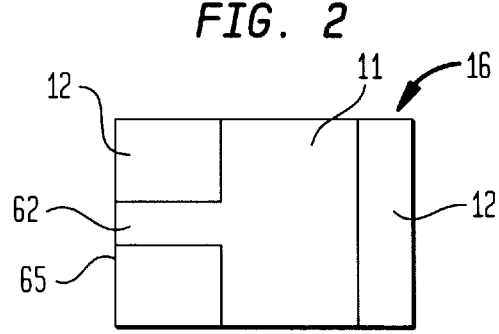
FIG. 2 is an elevational view of an intervertebral disc and associated vertebrae, of FIG. 1, from which the nucleus has been removed.
Figure 3:
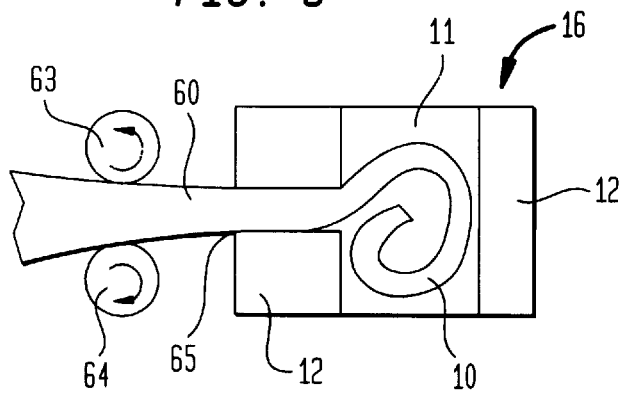
FIG. 3 is an elevational view, of the disc of FIG. 2 with the partially hydrated xerogel prosthetic nucleus of the present invention being implanted therein.

Referring to FIGS. 1 through 3, in the preferred embodiment the hydrogel prosthetic nucleus of the present invention, generally denoted as 10, conforms, when hydrated to its EWC, to the general shape of the natural nucleus. The prosthetic nucleus is implanted in the disc 12 of the vertebrae 14 and is surrounded by the natural annulus 16. Vertebral end plates 20 and 22, as shown in FIG. 1, cover the superior and inferior faces of nucleus 10 respectively.

Hydrogels useful in the practice of the invention include lightly cross-linked biocompatible homopolymers and copolymers of hydrophilic monomers such as 2-hydroxyalkyl acrylates and methacrylates, e.g., 2-hydroxyethyl methacrylate (HEMA); N-vinyl monomers, for example, N-vinyl-2-pyrrolidone (N-VP); ethylenically unsaturated acids, for example, methacrylic acid (MA) and ethylenically unsaturated bases such as 2-(diethylamino) ethyl methacrylate (DEAEMA). The copolymers may further include residues from non-hydrophilic monomers such as alkyl methacrylates, for example, methyl methacrylate (MMA), and the like. The cross-linked polymers are formed, by known methods, in the presence of cross-linking agents, such as ethyleneglycol dimethacrylate and methylenebis (acrylamide), and initiators such as 2,2-azobis (isobutyronitrile, benzoyl peroxide, and the like, and radiation such as UV and γ-ray.

Methods for the preparation of these polymers and copolymers is well known to the art. The EWC of these hydrogels can vary, e.g., from about 38% for Polymacon™ (poly HEMA) to about 79% for Lidofilcon™ B (a copolymer of N-VP and MMA) under ambient conditions.

Another type of hydrogel, useful in the practice of the invention, is illustrated by HYPAN™ and poly(vinyl alcohol) (PVA) hydrogels. These hydrogels, unlike the aforementioned hydrogels, are not cross-linked. Their insolubility in aqueous media is due to their partially crystalline structures. HYPAN™ is a partially hydrolyzed polyacrylonitrile. It has a multiblock copolymer (MBC) structure comprising hard crystalline nitrile blocks, which provide the hydrogel with good mechanical properties, and soft amorphous hydrophilic blocks to provide the hydrogel with good water binding capability. The methods of preparing HYPAN™ hydrogels of different water contents and mechanical properties have been disclosed in the U.S. Pat. Nos. 4,337,327, 4,370,451, 4,331,783; 4,369,294; 4,420,589; 4,379,874 and 4,631,188. The pre-nuclear forms of this material, for use in this invention, can be prepared by melt processing using solvents such as DMF and DMSO, as melting aids or by solution processing.

A preferred hydrogel for use in the practice of this invention is highly hydrolyzed crystalline poly(vinyl alcohol) (PVA). The amount of hydrolyzation may be between 95 and 100 percent depending on the desired EWC which will be from about 60% to about 90%. Generally, the final hydrogel water content increases with decreasing hydrolyzation of the initial PVA which results in decreased crystallinity.

Partialy crystalline PVA hydrogels may be prepared, from commercially available PVA powders, by any of the methods known to the art. Preferably, they are prepared by the method disclosed in the U.S. Pat. No. 4,663,358, the teachings of which are incorporated herein by reference. Typically, 10–15% PVA powder is mixed with a solvent, such as water, dimethyl sulfoxide (DMSO), ethylene glycol and mixtures thereof. A preferred solvent is 15% water in DMSO. The mixture is then heated at a temperature of about 100 to about 120° C., until a viscous solution is formed. The solution is then poured or injected into a tubular metal, glass or plastic mold and allowed to cool to below $-10°$ C., preferably to about $-20°$ C.

The solution is maintained at that temperature for several hours, preferably about 20 hours, during which time crystalization and, therefore, gelation of the PVA occurs. The shaped gel is soaked with several portions of water which are periodically replaced, over a period of at least two days, until all the organic solvent in the gel has been replaced by water. The hydrated gel can then be partially or completely dehydrated for implantation. The hydrogels thus prepared have EWC's between 60–90% and compressive strengths of at least 1 $MNm^{-2}$, preferably about 4 $MNm^{-2}$, when subject to the same constraints as the natural nucleus in an intervertebral disc.

Completion of the solvent exchange is determined by known methods. For instance, when the solvent is DMSO its removal, from the gel, is determined as follows:

50 $\mu L$ of a 0.01 N $KMnO_4$ solution are added to 50 mL aliquots of the water which has been separated from the gels. The presence of DMSO, in the water, will be indicated by disappearance of the characteristic pink color of the $KMnO_4$. When the DMSO has been completely removed the pink color will not disappear. This method has a detection limit of 0.3 ppm, for DMSO, when compared to a blank and 0.3 ppm aqueous DMSO standard.

In general, any hydrogel that can be used for biomedical purposes can be used as long as the hydrogel exhibits an EWC from about 30 to about 90% and a compressive strength of at least about 1 $MNm^{-2}$, preferably 4 $MNm^{-2}$, when subjected to the constraints of the annulus and end plates of the disc. A rod or tube made from these materials, in a dehydrated form, i.e., as xerogels, can be prepared either by cast molding or lathe cutting. In cast molding, the liquid monomer mixture, with initiator, is poured into a mold of predetermined shape and size, and cured. If desired, the casting mixture may include water, or another aqueous medium. Under those circumstances the resultant rod or tube will be partially hydrated, i.e., a hydrogel. In the case of lathe cutting, the xerogel can be prepared, in a similar manner to the above, in the form of a block or rod which is larger than needed to form the prosthetic nucleus. The xerogel is then cut to the shape and size required for implantation into the disc cavity. In both cases, the hydrogel expansion factor, due to polymer swelling upon hydration, has to be taken into account in designing the mold or in cutting the block, rod or tube.

The prosthesis is prepared by inserting at least one xerogel rod or tube, as described above, into the disc cavity through an opening, or window in the annulus. The xerogel can, if desired, be partially hydrated. In the practice of this invention, as illustrated in FIGS. 1–6, a xerogel rod 60 is inserted into cavity 61 through window 62 in the annulus 16. The insertion may be effected manually or, as shown in FIG. 3, by passage between pairs of rollers 63 & 64, rotating in opposite directions. When the desired amount of hydrogel has been passed into the cavity and window, past opening 65 in the annulus, the tail 66 of the rod 60 is pushed into the cavity 61. Body fluids which are present in, or enter, the cavity 61 are absorbed by the hydrogel rod 60 which expands to fill the cavity 61. These processes are shown in FIGS. 4–6 wherein the hydrogel is shown at increasing water contents, up to its EWC, and, therefore, increasing extents of expansion. FIG. 6 shows the rod at its EWC, and maximum expansion, whereby the hydrogel 10 has filled, and taken the shape of, the cavity 61.

The exact size of the prosthetic nucleus, at its EWC, can be varied for different individuals. A typical size of an adult nucleus is 2 cm in the semi-minor axis, 4 cm in the semi-major axis and 1.2 cm in thickness.

The major advantages of the elongated rod or tube design is that the incision area in the annulus can be reduced and it is easier to manipulate the implants during surgery.

The surfaces of the implants can either be smooth or have transverse grooves (not shown) to increase the stability of the prostheses in the disc cavities.

The hydrogels of the present invention have a much higher structural integrity than the natural nucleus, i.e., they are deformed with greater difficulty under a mechanical compressive load (shaped gel vs loose gel). That is because, unlike the loose gel of the natural nucleus, the shaped gel has shape memory due to the cross-linking or strong hydrogen bonding in the polymer matrix. However, it would still have extensive lateral bulging under high compressive load if there were no boundaries to constrain the deformation. Because use of the present invention does not involve removal of the disc annulus and/or end-plates, the lateral bulging of the hydrogel nucleus will be restricted by the restoring forces of the stretched fibers. Also, due to its superior structural integrity, the hydrogel nucleus will not herniate or bulge through the previously herniated areas or the incision which was made to remove the degenerated nucleus.

Since the natural nucleus is also, primarily, a hydrogel the implanted prosthetic nucleus can easily restore all the biomechanical functions of the nucleus which had been removed. Unlike the prior art prosthetic discs, the hydrogel nucleus of the present invention will restore the viscoelastic behavior of the disc due to the water binding capability of the prosthetic hydrogel.

The implantation of a prosthetic nucleus 10 can be performed in conjunction with a discectomy or chemonucleaylsis. Because the properties of the prosthetic nucleus of the present invention are similar to those of the nucleus material, the herniated nucleus can be partially or totally replaced by the hydrogel prosthetic nucleus. Due to the small size of the prosthesis it can be implanted into the disc by means of a posterior lateral approach, thereby significantly reducing the difficulty and the risk of the operation.

The volume of a hydrogel nucleus of about 80% EWC will be reduced by about 80% (to about 20% of its original volume) when dehydrated. Consequently, the surgeon does not need to jack apart the vertebrae adjacent to a damaged disc as required by, for example, the device disclosed in U.S. Pat. No. 4,772,287. The height of the dehydrated prosthetic nucleus, when inserted, is smaller than the disc space. Furthermore, the rigidity of the dehydrated prosthetic nucleus will help the surgeons to manipulate the prosthetic nucleus during the operation. After implantation, the hydrogel nucleus of the present invention swells in the body to a predetermined height which is enough to maintain the space between the vertebral body. The swelling process normally takes several hours to two days depending on the size of the prosthetic nucleus and type of hydrogel.

EXAMPLE 15 g PVA powder, having a molecular weight about 78000 and about 99.7% hydrolysed (Cat. No. 15129, Polysciences Inc., Warrington, Pa.), was mixed with 85 mL of a solvent comprising 15% water in DMSO. The mixture was heated at about 110° C. until a homogenous viscous solution formed. The solution was poured into a tubular glass mold of 30 mm length and 8 mm inner diameter. The solution was cooled to about −20° C. and kept at that temperature for about 20 hours whereby the PVA crystallized and formed a gel rod. The rod was removed from the mold and washed with water until all of the DMSO had been removed therefrom. The water content of the rod was 74%.

The above Example, to which many changes and modifications may be made, is for illustrative purposes only and is not intended to limit the spirit and scope of the invention which is defined by the claims.

We claim:

1. A prosthetic nucleus implant comprising before implantation at least one elongate, partially hydrated hydrogel member having a cross-sectional diameter of between about 2 mm and about 10 mm, the member sized and configured (a) to fold upon itself a plurality of times within a nucleus cavity upon insertion therein to only partially fill the cavity, and (b) subsequently upon an increase in hydration to essentially fill and conform to the shape of the cavity.

2. The prosthetic nucleus of claim 1 sized and configured upon an increase in hydration to its equilibrium water content to essentially fill and conform to the shape of the cavity.

3. The prosthetic nucleus of claim 1 wherein the equilibrium water content of the hydrogel is from about 30 to about 90%.

4. The prosthetic nucleus of claim 3 wherein the equilibrium water content of the hydrogel is from about 60 to about 80%.

5. The prosthetic nucleus of claim 2 wherein the partially hydrated member has a volume of 10–70% of the volume of the hydrogel at its equilibrium water content.

6. The prosthetic nucleus of claim 1 wherein the diameter of the partially hydrated member is from about 4 to about 8 mm.

7. The prosthetic nucleus of claim 1 consisting of only a single member.

8. The prosthetic nucleus of claim 1 consisting of a plurality of members.

9. The prosthetic nucleus of claim 1 wherein the hydrogel comprises PVA.

10. The prosthetic nucleus of claim 1 wherein the hydrogel is prepared by the homo- or co-polymerization of hydrophilic monomer, selected from the group consisting of N-vinyl monomers, hydroxyalkyl acrylates, hydroxyalkyl methacrylates, ethylenically unsaturated acids, ethylenically unsaturated bases, and their salts and mixtures thereof, in the presence of a cross-linking monomer containing at least two ethylenically unsaturated sites.

11. The prosthetic nucleus of claim 1 wherein the hydrogel comprises partially hydrolyzed polyacrylonitrile.

12. The prosthetic nucleus of claim 10 wherein the cross-linking monomer is ethyleneglycol dimethacrylate.

13. The prosthetic nucleus of claim 10 wherein said hydroxyalkyl methacrylate is 2-hydroxyethyl methacrylate; said N-vinyl monomer is N-vinyl-2-pyrrolidone; said ethylenically unsaturated acid is methacrylic acid; said ethylenically unsaturated base is 2-(diethylamino)ethyl methacrylate, and said cross-linking monomer is ethyleneglycol dimethacrylate.

14. The prosthetic nucleus of claim 13 wherein said copolymer is further formed by copolymerizing with at least one non-hydrophilic monomer.

15. The prosthetic nucleus of claim 14 wherein at least one of said non-hydrophilic monomers is an alkyl methacrylate.

16. The prosthetic nucleus of claim 1 wherein the hydrogel has a compressive strength of at least 1 MNm-2 when subjected to the constraints of the annulus and end plates of the disc.

17. The prosthetic nucleus of claim 16 wherein the hydrogel has a compressive strength of at least 4 MNm-2.

18. The prosthetic nucleus of claim 1 wherein the member is made of a homogeneous hydrogel.

19. A prosthetic nucleus implant means for filling an intervertebral disc nucleus cavity, the means consisting of an elongate, partially hydrated hydrogel member for (a) folding upon itself a plurality of times into said cavity upon insertion therein to only partially fill the cavity, and (b) subsequently upon an increase in hydration to essentially fill and conform to the shape of the cavity.

* * * * *

UNITED STATES PATENT AND TRADEMARK OFFICE
CERTIFICATE OF CORRECTION

PATENT NO. : 5,976,186
DATED : November 2, 1999
INVENTOR(S) : Bao et al.

It is certified that error appears in the above-indentified patent and that said Letters Patent is hereby corrected as shown below:

Column 9, line 11, insert a space between "95" and "and".
Column 11, line 5, "1" should read --2--.
Column 12, line 15, "monomer" should read --monomers--.
Column 12, line 15, cancel the ",".

Signed and Sealed this

Third Day of April, 2001

*Attest:*

NICHOLAS P. GODICI

*Attesting Officer*  *Acting Director of the United States Patent and Trademark Office*